United States Patent [19]
Aleksey

[11] Patent Number: 5,865,622
[45] Date of Patent: Feb. 2, 1999

[54] SYSTEM FOR ATTACHING A DENTAL PROSTHESIS TO A DENTAL IMPLANT

[76] Inventor: Brodsky Aleksey, 2401 Brigham St., Brooklyn, N.Y. 11235

[21] Appl. No.: 892,087

[22] Filed: Jul. 14, 1997

[51] Int. Cl.$^6$ .................................................. A61C 13/225
[52] U.S. Cl. .......................................... 433/177; 433/173
[58] Field of Search ..................................... 433/172, 173, 433/174, 175, 176, 177

[56]     References Cited

U.S. PATENT DOCUMENTS

| 2,599,044 | 6/1952 | Brennan | 433/173 |
| 2,644,231 | 7/1953 | Brennan | 433/173 |
| 5,468,150 | 11/1995 | Brammann | 433/173 |

FOREIGN PATENT DOCUMENTS

| 3812536 | 11/1989 | Germany | 433/177 |
| 4112200 | 6/1993 | Germany | 433/174 |

Primary Examiner—Cary E. O'Connor
Attorney, Agent, or Firm—Ilya Zborovsky

[57]          ABSTRACT

A system for attaching a dental prosthesis to a dental implant has a first element which is fixedly connectable with the dental implant, a second element which is fixedly connectable with the dental prosthesis, at least one of the elements being provided with elastic means which elastically engage a part of the other of the elements so as to retain the elements together with one another and therefore to fix the dental prosthesis on the dental implant, and a releasing element extending outwardly of the dental prosthesis and actuatable by a user so as to displace the elastically engaging means and disengage the one element from the part of the other element so as to allow easy removal of the one element together with the prosthesis from the other element connected with the dental implant.

2 Claims, 2 Drawing Sheets

SYSTEM FOR ATTACHING A DENTAL PROSTHESIS TO A DENTAL IMPLANT

BACKGROUND OF THE INVENTION

The present invention relates to a system for attaching a dental prosthesis to a dental implant.

Systems of the above mentioned general type are known in the art. The known systems are designed so that when a dental prosthesis is attached to a dental implant, it cannot be easily removed from the implant in the event any problems with the dental prosthesis or surrounding area of a patient's mouth. It is necessary to destroy an existing prosthesis and to install a new one. In other instances the removal is possible, by can be done only by a dentist. Also, easy hygienic maintenance of the prosthesis and implant or tooth abutment is not possible.

SUMMARY OF THE INVENTION

Accordingly, it is an object of the present invention to provide a system for attaching a dental prosthesis to a dental implant which is a further improvement of the inventive systems.

In keeping with these objects and with others which will become apparent hereinafter, one feature of present invention resides, briefly stated, to a system for attaching a dental prosthesis to a dental implant which has a first element stationarily fixable to a dental implant, a second element stationarily connectable with a dental prosthesis, means for elastically engaging said second element with said first element so that one of said elements snaps over the other of said elements, and means for elastically displacing at least a portion of said elastically engaging means so as to disengage said first element and said second element from one another and to allow easy removal of said first element with the dental prosthesis from said second element connected with the dental implant.

When the system is designed in accordance with present invention, it allows easy removal of the dental prosthesis from the dental implant for dental work as well as for hygienic maintenance.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

Figure 1:
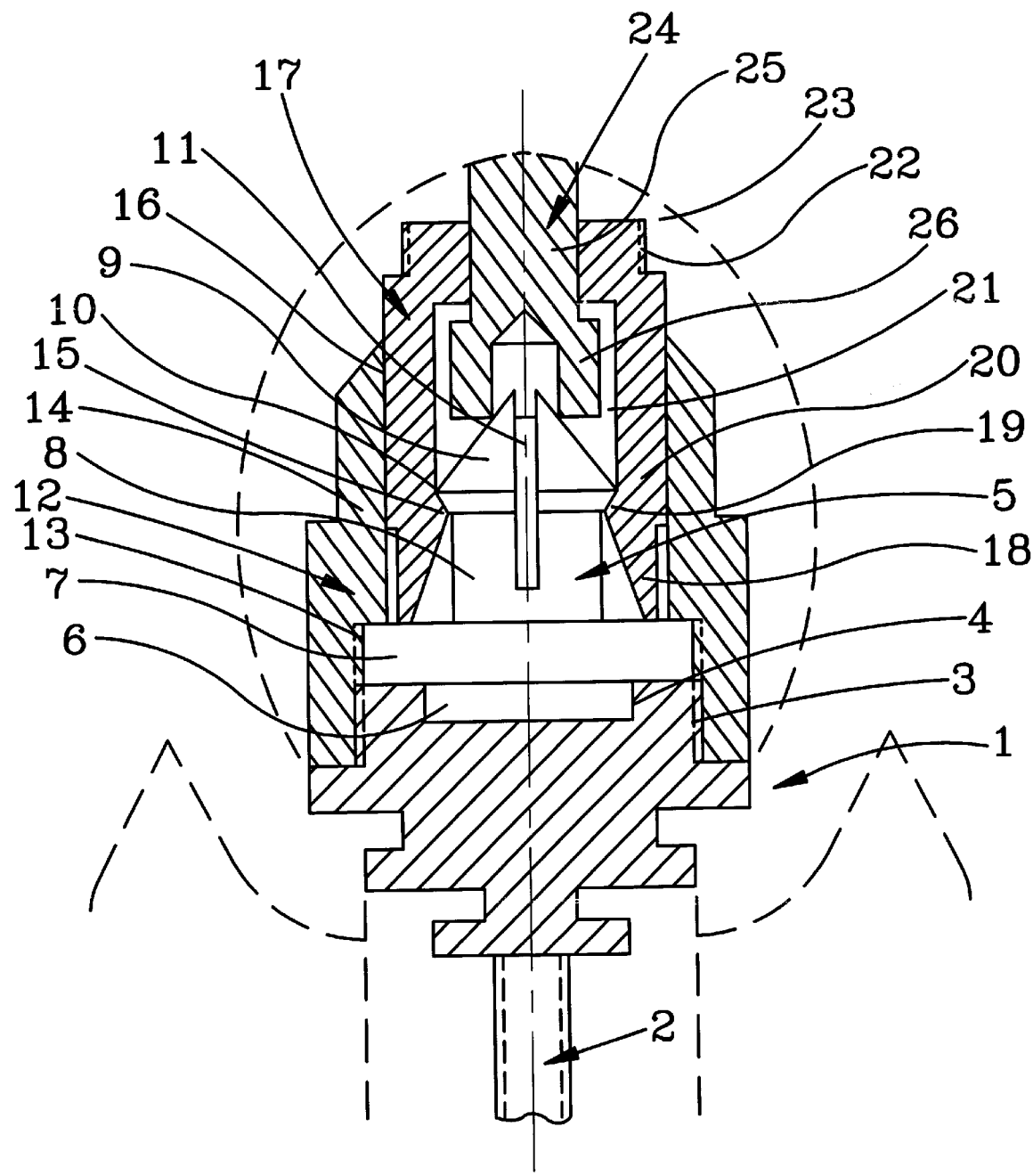
FIG. 1 is a view showing a system for attaching a dental prosthesis to a dental implant in accordance with a first embodiment of the present invention.

A system in accordance with present invention has a first element formed as a base identified as a whole with reference numeral 1. The base 1 includes a series of attached metal rings of varying diameters and is connected with a standard implant screw 2 which extends through it to attach the base 1 to the implant by screwing the screw 2 into the implant. The portions of the different diameters allow retention of the base 1 because it is either waxed or cast to a standard castable plastic cylinder abutment or soldered to a standard metal abutment cylinder. The top ring of the element 1 is provided with an external thread 3 and an internal hole 4.

The system further has a locking element which is identified with a reference numeral 5. The locking element 5 has a lower cylindrical portion 6 insertable into the hole 4 of the element 1, a flange 7, a cylindrical portion 8, and a conical head 9 forming a radially outwardly projecting shoulder 10 with a diameter greater than the diameter of the cylindrical portion 8. A slot 11 extends through the head 9 and the cylindrical portion 8. A securing ring 12 has a lower hollow part 13 screwable on the thread 3 of the upper most ring of the base 1 and an upper stepped part 14 which forms a shoulder 15 for retaining the cylindrical portions 7 of the locking element 5 and an inner surface 16. A second securing ring 17 has a lower ring portion 18 with a shoulder 19 located under the shoulder 8 of the locking element 5 in the locked position, and an upper portion 20 with a central opening 21 and a threaded projection 22 screwable into a dental implant 23. A release element 24 has a central portion 25 extending through the opening 21 of the securing ring 17, and a lower portion 26 provided with a central opening 27 and surrounding partially the conical portion 9 of the locking member 5. The central portion 25 of the release element 24 extends through the dental prosthesis to its outer surface.

The system operates in the following manner:

In the shown position, the dental prosthesis is axially mounted to the dental implant. In order to improve the dental prosthesis, a user pushes the release element 24 downwardly in FIG. 1 by a tool and the like. When the release element 24 is pushed down, it compresses the conical portion 9 of the locking element 5 so that the shoulder 10 of the locking element 5 assumes a smaller diameter than the diameter of the shoulder 19 of the securing ring 17, and therefore the securing ring 17 together with the dental implant can be displaced upwardly and removed.

In order to again fix the prosthesis to the dental implant, the securing ring 17 with the dental prosthesis is pushed downwardly so that the shoulder 19 of the securing ring 17 engages again under the shoulder 10 of the cone 9 of the locking element 5.

In the system in accordance with the second embodiment, parts which are similar to the parts of the first embodiment are identified with the same reference numerals with addition of primes. Here the second securing ring 17' is provided with a radially inner projection 31 which engages into a groove 32 of the locking element 5'. A releasing element 24' extends through the interior of the locking element 5' transversely to the axis of the system.

Figure 2:
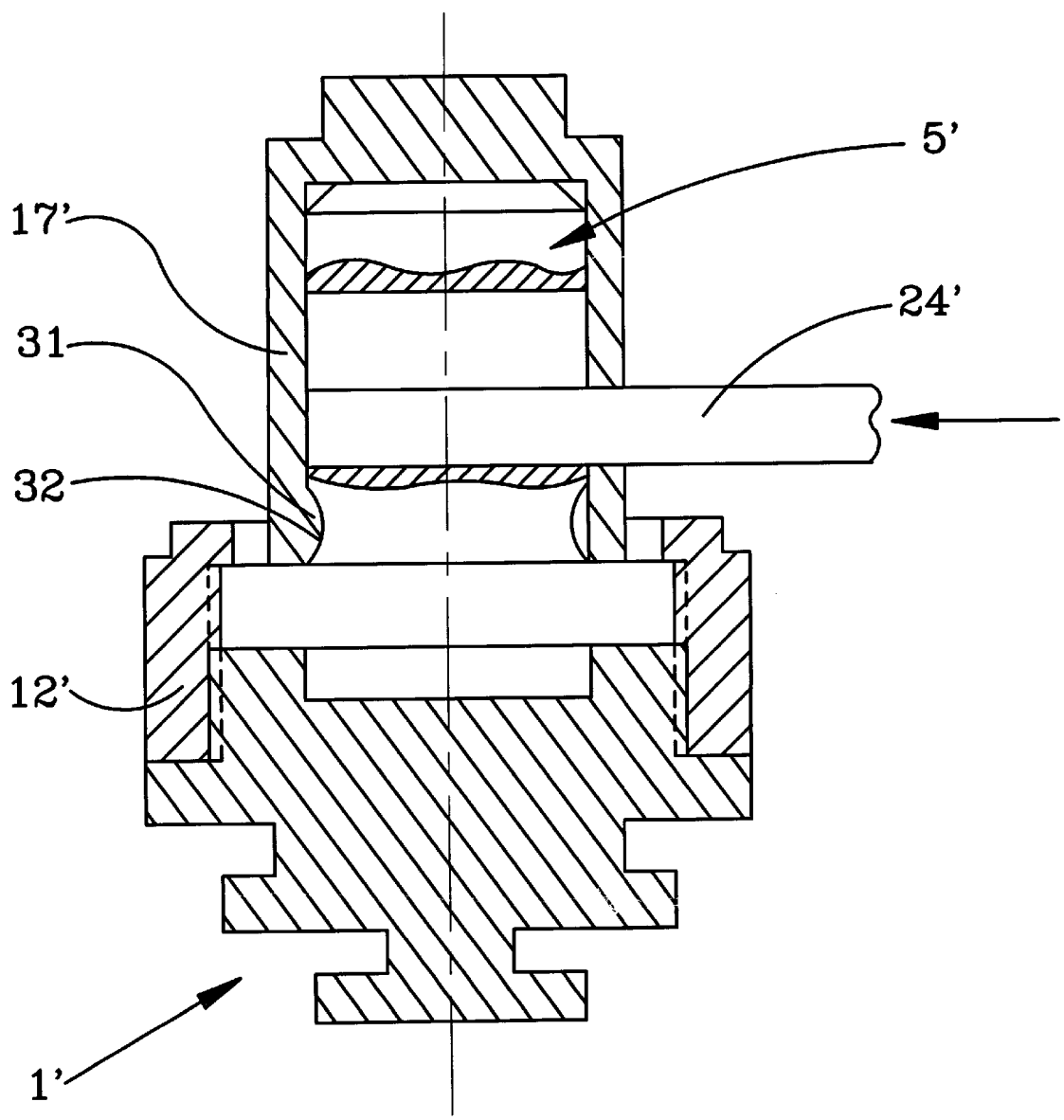
FIG. 2 is a view showing a system of attaching the dental prosthesis to the dental implant in accordance with the second embodiment of the present invention.

In the position shown in FIG. 2, the projection 31 of the securing element 17' engages in the groove 32 of the locking element 5' and the securing element 17' with the dental prosthesis attached to it is fixed to the dental implant. In order to remove the dental prosthesis, the releasing element 24' is pushed by user transversely to the axis of the system so that the left wall of the securing ring 17 is displaced to the left, and the projection 31 of the securing element 17' disengages from the groove 32 of the locking element 5'. Thereafter, the securing element 17' together with the prosthesis can be removed by displacing the same upwardly.

It will be understood that each of the elements described above, or two or more together, may also find a useful application in other types of constructions differing from the types described above.

While the invention has been illustrated and described as embodied in dental system, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A system for attaching a dental prosthesis to a dental implant, comprising a first element which is fixedly connectable with the dental implant; a second element which is fixedly connectable with the dental prosthesis; at least one of said elements being provided with elastic means which elastically engage a part of the other of said elements so as to retain said elements together with one another and therefore to fix the dental prosthesis on the dental implant; and a releasing element extending outwardly of the dental prosthesis and actuable by a user so as to displace said elastically engaging means and disengage said one element from said part of said other element so as to allow easy removal of said one element together with said prosthesis from said other element connected with the dental implant, said part of said other element has a portion connected with said other element and another portion which is elastically compressible and expandable, so that when said other portion is expanded, said elastically engaging means engage said elastically compressible and expandable portion and retain said element together, while when said other portion is compressed said elastically engaging means disengage from said other portion and allow removal of said one element with said dental prosthesis from said other element connected with said dental implant, said elastically compressible and engageable part is formed as a cone having a central slot, said releasing element being movable in a direction from the dental prosthesis toward the dental implant so as to compress said part of said other element.

2. A system for attaching a dental prosthesis to a dental implant, comprising a first element which is fixedly connectable with the dental implant; a second element which is fixedly connectable with the dental prosthesis; at least one of said elements being provided with elastic means which elastically engage a part of the other of said elements so as to retain said elements together with one another and therefore to fix the dental prosthesis on the dental implant; and a releasing element extending outwardly of the dental prosthesis and actuable by a user so as to displace said elastically engaging means and disengage said one element from said part of said other element so as to allow easy removal of said one element together with said prosthesis from said other element connected with the dental implant, said part having a groove, said elastically engaging means including a projection formed in said second member and elastically engageable in said groove, said releasing element being formed as a bushing element extending transversely to a direction from the dental prosthesis to the dental implant and transversely pushing said projection from said groove so as to allow removal of said other element with the dental prosthesis from said one element connected with said dental implant.

\* \* \* \* \*